US012611371B2

(12) United States Patent
Zhou et al.

(10) Patent No.: US 12,611,371 B2
(45) Date of Patent: Apr. 28, 2026

(54) COMPOSITION COMPRISING NON-VOLATILE/VOLATILE OILS AND LIPOPHILIC DYES, METHODS AND USES THEREOF

(71) Applicant: L'Oreal, Paris (FR)

(72) Inventors: Xiaoyin Zhou, Pudong Shanghai (CN); Mona Zheng, Pudong Shanghai (CN); Amit Jayaswal, Pudong Shanghai (CN); Shuhong Yuan, Pudong Shanghai (CN); Chunyue Liu, Pudong Shanghai (CN)

(73) Assignee: L'Oreal, Paris (FR)

( * ) Notice: Subject to any disclaimer, the term of this patent is extended or adjusted under 35 U.S.C. 154(b) by 788 days.

(21) Appl. No.: 17/282,703

(22) PCT Filed: Oct. 3, 2018

(86) PCT No.: PCT/CN2018/109242

§ 371 (c)(1),
(2) Date: Apr. 2, 2021

(87) PCT Pub. No.: WO2020/069636

PCT Pub. Date: Apr. 9, 2020

(65) Prior Publication Data

US 2021/0378944 A1 Dec. 9, 2021

(51) Int. Cl.

| | |
|---|---|
| ***A61K 8/92*** | (2006.01) |
| ***A61K 8/31*** | (2006.01) |
| ***A61K 8/892*** | (2006.01) |
| ***A61K 8/895*** | (2006.01) |
| ***A61Q 5/06*** | (2006.01) |
| ***A61Q 5/12*** | (2006.01) |

(52) U.S. Cl.

CPC ................ *A61K 8/922* (2013.01); *A61K 8/31* (2013.01); *A61K 8/892* (2013.01); *A61K 8/895* (2013.01); *A61Q 5/065* (2013.01); *A61Q 5/12* (2013.01); *A61K 2800/31* (2013.01); *A61K 2800/43* (2013.01); *A61K 2800/594* (2013.01)

(58) Field of Classification Search

CPC .......... A61K 8/922; A61K 8/31; A61K 8/892; A61K 8/895; A61K 2800/31; A61K 2800/43; A61K 2800/594; A61Q 5/065; A61Q 5/12

See application file for complete search history.

(56) References Cited

U.S. PATENT DOCUMENTS

2005/0027051 A1* 2/2005 O'Brien ................ A61K 8/042 524/261
2012/0308498 A1* 12/2012 Hercouet ................ A61K 8/06 8/405

FOREIGN PATENT DOCUMENTS

| | | | |
|---|---|---|---|
| CN | 1636543 | 7/2005 | |
| CN | 102388107 | 11/2014 | |
| CN | 105662926 | 6/2016 | |
| JP | 2009184949 A | 8/2009 | |
| JP | 2014001206 A | 1/2014 | |
| JP | 2014227365 A | 12/2014 | |
| JP | 2015003886 A | 1/2015 | |
| WO | WO-2017050699 A1 * | 3/2017 | ............... A61K 8/31 |

OTHER PUBLICATIONS

International Search Report and Written Opinion for International Application No. PCT/CN2018/109242, filed Oct. 3, 2018, mailed Jul. 3, 2019 (8 pages).

* cited by examiner

*Primary Examiner* — Sean M Basquill
(74) *Attorney, Agent, or Firm* — CHRISTENSEN O'CONNOR JOHNSON KINDNESS PLLC

(57) ABSTRACT

Cosmetic composition comprising one or more particular non-volatile oils, one or more volatile oils and one or more lipophilic dyes, methods and uses thereof.

13 Claims, No Drawings

COMPOSITION COMPRISING NON-VOLATILE/VOLATILE OILS AND LIPOPHILIC DYES, METHODS AND USES THEREOF

The present invention relates to a composition comprising one or more particular non-volatile oils, one or more volatile oils and one or more lipophilic dyes.

The present invention also relates to a method for conditioning keratin fibres, in particular human keratin fibres such as the hair, comprising at least a step of applying onto said keratin fibres of a composition according to the invention.

The present invention also relates to the use of a composition according to the invention for conditioning keratin fibres, in particular human keratin fibres such as the hair.

The hair is generally damaged and weakened by the action of external atmospheric agents such as light, weather, and/or the action of mechanical or chemical treatments such as brushing, combing, dyeing, bleaching, permanent and/or straightening.

Thus, to overcome these drawbacks, it is common to resort to hair care implying the implementation of care compositions that can condition the hair following these treatments to give them shine, softness, suppleness, lightness, a natural touch and detangling properties.

However, these hair care compositions do not necessarily give complete satisfaction and can still be improved, especially with regard to the hair shine, the refreshing of the colour of the hair tips, and the definition of the hair curl (without frizz). In particular, the colour of the hair may remain dull and lose its liveliness over time.

Furthermore, the hair compositions of the prior art do not generally give rise to satisfaction with regard to the qualities of use (easy spreading of the composition, no stain on the skin), or in terms of remanence to different external agents (for examples shampoos, light, pollution).

There is therefore a real need to develop compositions which are also able to condition the keratin fibres, to refresh the colour of the hair tips, and to confer improved cosmetic properties to the keratin fibres (especially more shine), after one or more applications, without charge or weighting of the keratin fibres, while maintaining good qualities of use (ease of spreading of the composition on hair, no stain on the skin) and a good definition of the hair curl where necessary.

These aims are achieved by the present invention, one subject of which is a cosmetic composition comprising:

i) at least 5% by weight relative to the total weight of the composition, of one or more non-volatile oils chosen from esters of glycerol and of one or more identical or different, saturated or unsaturated, fatty acids containing 4 to 30 carbon atoms;

ii) at least 10% by weight relative to the total weight of the composition, of one or more volatile oils; and iii) one or more lipophilic dyes.

The composition according to the invention makes it possible to achieve the desired properties, inter alia in terms of integrity, quality and cosmeticity of the keratin fibres.

Particularly, the hair treated with the composition according to the invention is full of vitality, shiny and not dull.

Furthermore, the composition according to the invention makes it possible to obtain a good conditioning of the keratin fibres with a good definition of the hair curl (without frizz) and without charge or weighting of the hair, while maintaining good qualities of use (ease of spreading of the composition on hair, no stain on the skin nor on the hands).

Other characteristics and advantages of the invention will emerge more clearly on reading the description and the examples that follow.

In the present description and unless otherwise indicated:

- the limits of a range of values are included within this range, in particular in the expressions “of between . . . and . . . ” and “ranging from . . . to . . . ”;
- the expression “at least one” used in the present description is equivalent to the expression “one or more” and may be substituted for it.
- the term “oil” is intended to mean a fatty substance that is liquid at ambient temperature (25° C.) and atmospheric pressure (760 mmHg, i.e. $1.013\times10^5$ Pa). The oil may be volatile or non-volatile.
- the term “volatile oil” is intended to mean an oil that is capable of evaporating on contact with the skin or the keratin fibre in less than one hour, at ambient temperature and atmospheric pressure. The volatile oils of the invention are volatile cosmetic oils which are liquid at ambient temperature (25° C.) and which have a non-zero vapour pressure, at ambient temperature (25° C.) and atmospheric pressure ranging in particular from 0.13 Pa to 40000 Pa ($10^{-3}$ to 300 mmHg), in particular ranging from 1.3 Pa to 13000 Pa (0.01 to 100 mmHg) and more particularly ranging from 1.3 Pa to 1300 Pa (0.01 to 10 mmHg).
- the term “non-volatile oil” is intended to mean an oil that remains on the skin or the keratin fibre at ambient temperature (25° C.) and atmospheric pressure for at least several hours, and that in particular has a vapour pressure of less than $10^{-3}$ mmHg (0.13 Pa).
- by “silicone”, it means a polymer or an oligomer which comprises at least several —Si—O— units.
- by “non-volatile silicone oils”, it means a silicone as defined previously, liquid at ambient temperature (25° C.) and atmospheric pressure, and which remains on the skin or the keratin fibre at ambient temperature (25° C.) and atmospheric pressure for at least several hours, and which in particular has a vapour pressure of less than $10^{-3}$ mmHg (0.13 Pa).
- The term “hydrocarbon-based oil” means an oil mainly containing carbon and hydrogen atoms and possibly one or more functions chosen from hydroxyl, ester, ether and carboxylic functions. Generally, the oil has a viscosity of from 0.5 to 100000 mPa·s, preferably from 50 to 50 000 mPa·s and more preferably from 100 to 30000 mPa·s.
- The viscosity indicated thereafter are measured at a temperature of 25° C., using a viscometer Rheomat® RM 180 at a shear rate of 1 $s^{-1}$.

The Non-Volatile Oils i)

According to the invention, the composition comprises at least 5% by weight relative to the total weight of the composition, of one or more non-volatile oils i) chosen from esters of glycerol and of one or more identical or different, saturated or unsaturated, fatty acids containing 4 to 30 carbon atoms.

According to the invention, the identical or different, saturated or unsaturated, fatty acids may be substituted by one or more hydroxy radicals.

As examples of esters of glycerol and of one or more saturated or unsaturated fatty acids containing 4 to 30 carbon atoms that may be used in the invention, mention may be made of heptanoic or octanoic acid triglycerides, or else wheat germ oil, olive oil, sweet almond oil, palm oil, rapeseed oil, cottonseed oil, alfalfa oil, poppy seed oil, pumpkin seed oil, blackcurrant oil, evening primrose oil, millet oil, barley oil, *quinoa* oil, rye oil, coriander seed oil, limnanthes alba seed oil, nigella *sativa* seed oil, pentaclethra macroloba seed oil, *Adansonia digitata* seed oil, *Mauritia flexuosa* oil, *Lunaria annua* oil, pennycress oil, *Cuphea* oil, safflower oil, candlenut oil, passionflower oil, musk rose oil, sunflower oil, maize oil, soybean oil, marrow oil, grape seed oil, sesame oil, hazelnut oil, apricot kernel oil, macadamia *ternifolia* seed oil, castor oil, avocado oil, caprylic/capric acid triglycerides, such as those sold by the company Stearineries Dubois or those sold under the names Miglyol 810, 812 and 818 by the company Dynamit Nobel, jojoba oil or shea butter oil.

Preferably, the non-volatile oil(s) i) is/are chosen from esters of glycerol and of one or more identical or different, saturated or unsaturated, fatty acids containing 4 to 24 carbon atoms; more preferably from esters of glycerol and of one or more fatty acids containing 6 to 24 carbon atoms.

According to a preferred embodiment of the invention, the non-volatile oil(s) i) is/are chosen from caprylic/capric triglyceride, olive oil, macadamia *ternifolia* seed oil, castor oil, sunflower oil, soybean oil, sesame oil, apricot kernel oil, coriander seed oil, limnanthes alba seed oil, nigella *sativa* seed oil, pentaclethra macroloba seed oil, *Adansonia digitata* seed oil, *Mauritia flexuosa* oil, *Lunaria annua* oil, pennycress oil, *Cuphea* oil, and mixtures thereof; more preferably from the non-volatile oil i) is caprylic/capric triglyceride.

Preferably, the non-volatile oil(s) i) in the composition according to the invention represent(s) from 5 to 45% by weight; more preferably from 7 to 40% by weight; even more preferably from 10 to 35% by weight, relative to the total weight of the composition.

Preferably, the ester(s) of glycerol and of one or more identical or different, saturated or unsaturated, fatty acids containing 4 to 30 carbon atoms in the composition according to the invention represent(s) from 5 to 45% by weight; more preferably from 7 to 40% by weight; even more preferably from 10 to 35% by weight, relative to the total weight of the composition.

Preferably, when caprylic/capric triglyceride is present in the composition according to the invention, caprylic/capric triglyceride represents from 5 to 45% by weight; more preferably from 7 to 40% by weight; even more preferably from 10 to 35% by weight, relative to the total weight of the composition.

The Volatile Oils ii)

According to the invention, the composition comprises at least 10% by weight relative to the total weight of the composition, of one or more volatile oils ii).

Preferably, the volatile oil(s) ii) is/are chosen from hydrocarbon-based volatile oils, volatile silicone oils, and mixtures thereof.

As examples of volatile hydrocarbon-based volatile oils that may be used in the invention, mention may be made of volatile hydrocarbon-based oils chosen from hydrocarbon-based oils containing from 8 to 16 carbon atoms, and in particular $C_8$-$C_{16}$ isoalkanes of petroleum origin (also known as isoparaffins), for instance isododecane (also known as 2,2,4,4,6-pentamethylheptane), isodecane and isohexadecane, and for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used; volatile linear alkanes, such as those described in patent application DE 10 2008 012 457 from the company Cognis.

Preferably, the hydrocarbon-based volatile oil(s) is/are chosen from $C_8$-$C_{16}$ isoalkanes such as isododecane or isohexadecane; linear $C_8$-$C_{16}$ alkanes such as an undecane/tridecane mixture; and mixtures thereof.

As examples of volatile silicone oils that may be used in the invention, mention may be made of:

volatile linear alkyltrisiloxane oils of general formula (I):

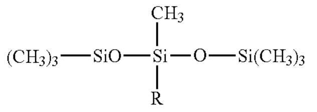

(I)

in which R represents an alkyl group comprising from 2 to 4 carbon atoms, one or more hydrogen atoms of which may be replaced with a fluorine or chlorine atom.

Among the oils of general formula (I), mention may be made of:

3-butyl-1,1,1,3,5,5,5-heptamethyltrisiloxane, 3-propyl-1,1,1,3,5,5,5-heptamethyltrisiloxane, and 3-ethyl-1,1,1,3,5,5,5-heptamethyltrisiloxane, corresponding to the oils of formula (I) for which R is, respectively, a butyl group, a propyl group or an ethyl group.

volatile linear or cyclic silicone oils different from the volatile linear alkyltrisiloxane oils of general formula (I) such as described above, especially those with a viscosity ≤8 centistokes ($8\times10^{-6}$ $m^2/s$) at 25° C. and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltri siloxane, decamethyltetrasiloxane and dodecamethylpentasiloxane.

Preferably, the volatile silicone oil(s) is/are chosen from octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof; more preferably the decamethylcyclopentasiloxane.

According to a preferred embodiment of the invention, the volatile oil(s) ii) is/are chosen from $C_8$-$C_{16}$ isoalkanes, linear $C_8$-$C_{16}$ alkanes, volatile linear alkyltrisiloxane oils of general formula (I) such as described previously, volatile linear or cyclic silicone oils different from the volatile linear alkyltrisiloxane oils of general formula (I) such as described previously, and mixtures thereof; more preferably chosen from isododecane or decamethylcyclopentasiloxane.

Preferably, the volatile oil(s) ii) in the composition according to the invention represent(s) from 10 to 98% by weight; more preferably from 20 to 95% by weight; even more preferably from 30 to 90% by weight, better still from 50 to 90% by weight, relative to the total weight of the composition.

Preferably, when the hydrocarbon-based volatile oil(s) is/are present in the composition according to the invention, the hydrocarbon-based volatile oil(s) represent(s) from 10 to 98% by weight; more preferably from 20 to 95% by weight; even more preferably from 30 to 90% by weight, better still from 50 to 90% by weight, relative to the total weight of the composition according to the invention.

Preferably, when isododecane is present in the composition according to the invention, isododecane represents from 10 to 98% by weight; more preferably from 20 to 95% by weight; even more preferably from 30 to 90% by weight, better still from 50 to 90% by weight, relative to the total weight of the composition according to the invention.

Preferably, when the volatile silicone oil(s) is/are present in the composition according to the invention, the volatile silicone oil(s) represent(s) from 10 to 98% by weight; more preferably from 20 to 95% by weight; even more preferably from 30 to 90% by weight, better still from 50 to 90% by weight, relative to the total weight of the composition according to the invention.

Preferably, when decamethylcyclopentasiloxane is present in the composition according to the invention, decamethylcyclopentasiloxane represents from 10 to 98% by weight; more preferably from 20 to 95% by weight; even more preferably from 30 to 90% by weight, better still from 50 to 90% by weight, relative to the total weight of the composition according to the invention.

According to a preferred embodiment of the invention, the composition according to the invention comprises a weight ratio of the content of non-volatile oil(s) i) to the content of the volatile oil(s) ii), which is between 0.01 and 10, more preferably inclusively between 0.01 and 2; even more preferably inclusively between 0.05 and 1; better still inclusively between 0.1 and 0.9.

The Lipophilic Dyes iii)

According to the invention, the composition comprises one or more lipophilic dyes iii).

Preferably, the lipophilic dye(s) iii) is/are chosen from natural or synthetic lipophilic dyes.

According to a preferred embodiment of the invention, the lipophilic dye(s) iii) is/are chosen from DC Red 17, DC Red 21, DC Red 27, DC Green 6, DC Yellow 11, DC Violet 2, DC Orange 5, Sudan Red, Sudan brown, quinoline yellow, annatto, curcumin, carotenes, xanthophylls, lipophilic green dyes and mixtures thereof.

Among the carotenes, we can mention in particular α-carotene, β-carotene, lycopene.

Among the carotenes, β-carotene will be used more particularly (CI 40800, CI 75130, Food Orange 5 or Natural Yellow 26). The β-carotene molecule is a chain consisting of 8 isoprenic units with alternating single and double bonds, and has the following formula:

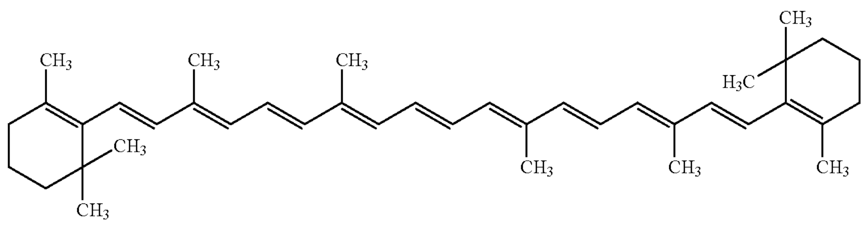 [SMILES: CC1=C(/C=C/C(C)=C/C=C/C(C)=C/C=C/C=C(C)/C=C/C=C(C)/C=C/C2=C(C)CCCC2(C)C)C(C)(C)CCC1]

β-carotene is found in some fruits and vegetables: pepper, carrot, spinach, lettuce, tomato, sweet potato, broccoli, cantaloupe, squash, apricot. β-carotene can be obtained either by extraction, by synthesis or by biotechnological means. Natural β-carotene comes mainly from red palm oil and alfalfa and also from carrot oil.

According to a particularly preferred form, β-carotene will be used in the form of a dispersion in an oil such as a 30% dispersion of β-carotene in sunflower oil, such as the product sold under the trade name 409185 CAROTENE-DISPERSION NATURAL 30% L-OS E-160A manufactured by LCW—Sensient Cosmetic Technologies or the 30% dispersion in corn oil, such as the product sold under the trade name 30% Beta Carotene FS (Fluid Suspension) by the company DSM Nutritional Products, Inc.

Among the xanthophylls, we can mention in particular:

astaxanthin antheraxanthin citranaxanthine cryptoxanthin canthaxanthin diatomoxanthine flavoxanthine fucoxanthin lutein rhodoxanthin rubixanthine siphonaxanthine violaxanthine zeaxanthin Among the xanthophylls, there will be used more particularly the astaxanthin of formula:

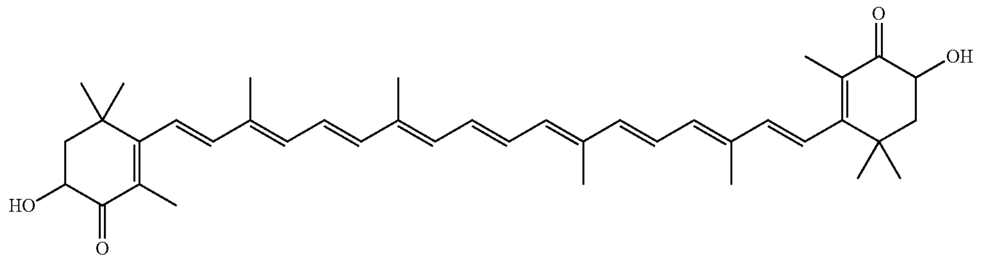 [SMILES: CC1=C(/C=C/C(C)=C/C=C/C(C)=C/C=C/C=C(C)/C=C/C=C(C)/C=C/C2=C(C)C(=O)C(O)CC2(C)C)C(C)(C)CC(O)C1=O]

Astaxanthin is usually extracted from the alga *Haematococcus pluvialis*. It belongs to the family of terpenes, and is part of the phytochemicals. It is present in crustaceans (crabs, shrimps, lobster, crayfish, lobsters), salmon, sea bream and in the feathers of some birds. It can be considered as the ultimate term of a series of hydroxylations and oxidations from β-carotene.

According to a particularly preferred form, the astaxanthin will be used in the form of a dispersion in an oil such as a 5% dispersion of astaxanthin from *Euphausia Superba* in a caprylic/capric triglyceride mixture such as the product sold under the name Commercial ASTAX-S by the company ITANO REFRIGERATED FOOD, or a dispersion of 4.5-7% asthaxanthin in a caprylic/capric triglyceride mixture extracted from seaweed *Haematococcus pluvialis* as the Product Sold under the trade name ASTA TROL-X by FUJI COLOR, or the product sold under the trade name BIOASTIN 5% OLEORESIN by the company CYANOTECH.

It is also possible to mention asthaxanthin dispersions in a caprylic/capric triglyceride mixture extracted from *Haematococcus pluvialis* algae, such as AM Asta-SOD commercial products from Athena Co LTD; the Astaxanthin-5C and Astaxanthin-PC1 commercial products by *Oryza* Oil & Fat Chemical Co.

By "green dye" is meant any organic cosmetic or dermatological dye capable of absorbing light radiation of wavelength between 400 and 500 nm and those of wavelength between 600 and 700 nm.

Among the lipophilic green dyes that may be used according to the invention, mention may be made of quinizarin (Ceres Green BB, D&C Green No. 6, CI 61565, 1,4-Di-p-toluidoanthraquinone, Green No. 202, Quinizarin Green SS) of formula:

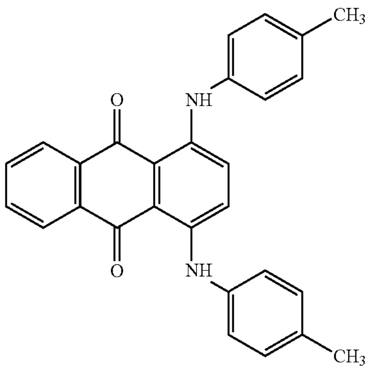 [SMILES: Cc1ccc(Nc2ccc(Nc3ccc(C)cc3)c3c2C(=O)c2ccccc2C3=O)cc1]

such as the product sold under the trade name D&C Green 6 K7016 by LCW—Sensient Cosmetic Technologies.

Among the lipophilic green dyes, chlorophylls may also be mentioned more preferably. Chlorophylls consist of four ring-shaped pyrrole rings as a complex of a divalent cation and a long-chain alcohol such as phytol. There are several forms of chlorophyll differentiable according to their chemical structure. Chlorophyll exists in all plants, chlorophyll b is found in higher plants and green algae. Two other variants exist in brown algae and some cyanobacteria, respectively chlorophylls c and d. The divalent cation (s) present in chlorophylls are generally chosen from alkali metals such as sodium or potassium, alkaline earth metals such as calcium, magnesium and transition metals such as copper and iron or mixtures thereof.

It is preferable to use a chlorophyll in the form of a copper complex and more particularly in the form of a dispersion in an oil such as sunflower oil or grape seed oil, such as the commercial products CHLOROPHYLLE LIPOSOLUBLE W 7208, 503509 COPPER CHLOROPHYLL 15% L-OS and CHLOROPHYLLE LIPOSOLUBLE W 7208 sold by LCW—Sensient Cosmetic Technologies.

According to one particular form of the invention, the lipophilic dye(s) may be used in encapsulated form.

According to a particularly preferred embodiment of the invention, the composition according to the invention comprises lipophilic dye(s) iii) chosen from D&C Violet 2 (C.I. 60725), beta-carotene (C.I. 75130), Green 6 (C.I. 61565), astaxanthin, and mixtures thereof.

Preferably, the lipophilic dye(s) iii) in the composition according to the invention represents from 0.0001 to 10% by weight, more preferably from 0.001 to 5% by weight, even more preferably from 0.001 to 1% by weight, relative to the total weight of the composition.

According to a particular embodiment of the invention, the composition according to the invention comprises a mixture of beta-carotene (C.I. 75130) and D&C Violet 2 (C.I. 60725); preferably in a total content representing from 0.001 to 0.1% by weight, relative to the total weight of the composition.

According to another particular embodiment of the invention, the composition according to the invention comprises a mixture of astaxanthin and D&C Violet 2 (C.I. 60725); preferably in a total content representing from 0.001 to 0.1% by weight, relative to the total weight of the composition.

According to another particular embodiment of the invention, the composition according to the invention comprises a mixture of Green 6 (C.I. 61565), astaxanthin and D&C Violet 2 (C.I. 60725); preferably in a total content representing from 0.001 to 0.1% by weight, relative to the total weight of the composition.

The Non-Volatile Silicone Oils

According to the invention, the composition can optionally further comprise one or more non-volatile silicones oils.

Preferably, the non-volatile silicones oil(s) is/are chosen from non-volatile non-phenyl silicone oils, non-volatile phenyl silicone oil, and mixtures thereof.

The term "non-phenyl silicone oil" denotes a silicone oil not bearing any phenyl substituents.

Representative examples of these non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups.

It should be noted that "dimethicone" (INCI name) corresponds to a polydimethylsiloxane (chemical name).

The non-volatile non-phenyl silicone oil is preferably chosen from non-volatile dimethicone oils.

In particular, these oils can be chosen from the following non-volatile oils:

- polydimethylsiloxanes (PDMSs),
- PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference Abil Wax 9801 from Evonik Goldschmidt,
- PDMSs comprising aliphatic groups, or functional groups such as hydroxyl, thiol and/or amine groups,
- polyalkylmethylsiloxanes substituted with functional groups such as hydroxyl, thiol and/or amine groups,
- polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular $C_2$-$C_{24}$ alkyl groups, and/or functional groups such as hydroxyl, thiol and/or amine groups.

The non-phenyl silicone oil may be chosen in particular from silicones of formula (S-I):

(S-I)

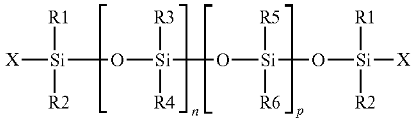

in which:

- $R_1$, $R_2$, $R_5$ and $R_6$ are, together or separately, an alkyl radical containing from 1 to 6 carbon atoms,
- $R_3$ and $R_4$ are, together or separately, an alkyl radical containing from 1 to 6 carbon atoms, a vinyl radical, an amine radical or a hydroxyl radical,
- X is an alkyl radical containing from 1 to 6 carbon atoms, a hydroxyl radical or an amine radical,
- n and p are integers chosen so as to have a fluid compound, in particular of which the viscosity at 25° C. is between 9 centistokes (cSt) ($9\times10^{-6}$ $m^2/s$) and 800000 cSt.

As non-volatile non-phenyl silicone oils which can be used according to the invention, mention may be made of those for which:

- the substituents $R_1$ to $R_6$ and X represent a methyl group, and p and n are such that the viscosity is 500000 cSt at 25° C., for example the product sold under the name SE30 by the company General Electric, the product sold under the name AK 500000 by the company Wacker, the product sold under the name Mirasil DM 500000 by the company Bluestar, and the product sold under the name Dow Corning 200 Fluid 500000 cSt by the company Dow Corning,
- the substituents $R_1$ to $R_6$ and X represent a methyl group, and p and n are such that the viscosity is 60000 cSt at 25° C., for example the product sold under the name Dow Corning 200 Fluid 60000 CS by the company Dow Corning, and the product sold under the name Wacker Belsil DM 60000 by the company Wacker,
- the substituents $R_1$ to $R_6$ and X represent a methyl group, and p and n are such that the viscosity is 100 cSt or 350 cSt at 25° C., for example the products sold respectively under the names Belsil DM100 and Dow Corning 200 Fluid 350 CS by the company Dow Corning,
- the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

The expression "phenyl silicone oil" denotes a silicone oil bearing at least one phenyl substituent.

The non-volatile phenyl silicone oils may be chosen from those also having at least one dimethicone fragment, or from those not having one.

According to the invention, a dimethicone fragment corresponds to the following unit:

$$—Si(CH_3)_2—O—.$$

The non-volatile phenyl silicone oil may thus be chosen from:

a) phenyl silicone oils optionally having a dimethicone fragment corresponding to formula (S-II) below:

(S-II)

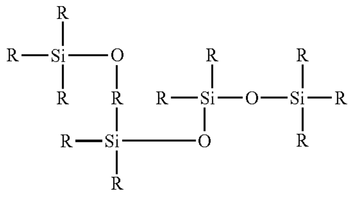

in which the groups R, which are monovalent or divalent, represent, independently of each other, a methyl or a phenyl, with the proviso that at least one group R represents a phenyl.

Preferably, in this formula, the phenyl silicone oil comprises at least three, for example at least four, at least five or at least six, phenyl groups.

b) phenyl silicone oils optionally having a dimethicone fragment corresponding to formula (S-III) below:

(S-III)

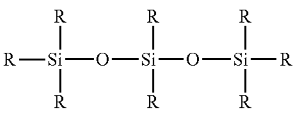

in which the groups R represent, independently of each other, a methyl or a phenyl, with the proviso that at least one group R represents a phenyl.

Preferably, in this formula, the compound of formula (S-III) comprises at least three, for example at least four or at least five, phenyl groups.

Mixtures of different phenylorganopolysiloxane compounds described above can be used.

Examples that may be mentioned include mixtures of triphenyl-, tetraphenyl- or pentaphenyl-organopolysiloxanes.

Among the compounds of formula (S-III), mention may be made more particularly of phenyl silicone oils not having any dimethicone fragments, corresponding to formula (S-III) in which at least 4 or at least 5 radicals R represent a phenyl radical, the remaining radicals representing methyls.

Such non-volatile phenyl silicone oils are preferably trimethylpentaphenyltrisiloxane or tetramethyltetraphenyltrisiloxane. They are in particular sold by Dow Corning under the reference PH-1555 HRI or Dow Corning 555 Cosmetic Fluid (chemical name: 1,3,5-trimethyl-1,1,3,5,5-pentaphenyltrisiloxane; INCI name: trimethylpentaphenyltrisiloxane), or the tetramethyltetraphenyltrisiloxane sold under the reference Dow Corning 554 Cosmetic Fluid by Dow Corning can also be used.

They correspond in particular to formulae (S-IV) and (S-IV') below:

(S-IV)

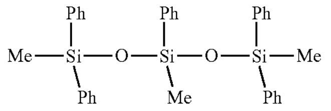

(S-IV')

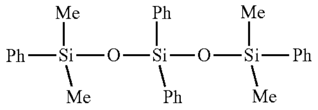

in which Me represents methyl and Ph represents phenyl.

c) phenyl silicone oils having at least one dimethicone fragment corresponding to formula (S-V) below:

(S-V)

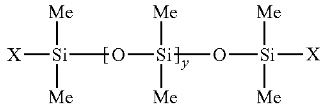

in which Me represents methyl, y is between 1 and 1000 and X represents $—CH_2—CH(CH_3)(Ph)$.

d) phenyl silicone oils corresponding to formula (S-VI) below, and mixtures thereof:

(S-VI)

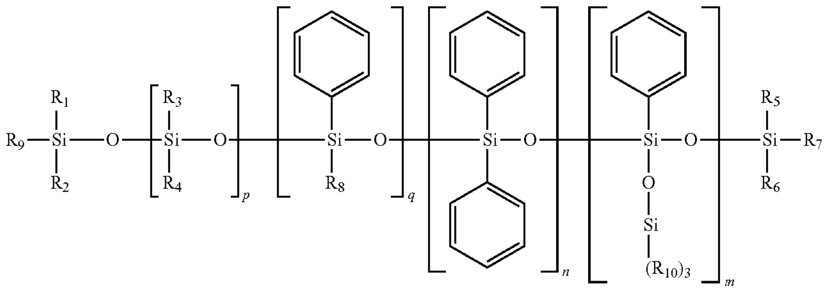

in which:

$R_1$ to $R_{10}$, independently of each other, are saturated or unsaturated, linear, cyclic or branched $C_1$-$C_{30}$ hydrocarbon-based radicals, m, n, p and q are, independently of each other, integers between 0 and 900, with the proviso that the sum m+n+q is other than 0.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$, independently of each other, represent a saturated or unsaturated, preferably saturated, linear or branched $C_1$-$C_{30}$ hydrocarbon-based radical, and in particular a preferably saturated, $C_1$-$C_{20}$, in particular $C_1$-$C_{18}$, hydrocarbon-based radical, or a monocyclic or polycyclic $C_6$-$C_{14}$, and in particular $C_{10}$-$C_{13}$, aryl radical, or an aralkyl radical, the alkyl part of which is preferably $C_1$-$C_3$ alkyl.

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may in particular be identical, and in addition may be a methyl radical.

According to a particular embodiment of formula (S-VI), mention may be made of:

i) phenyl silicone oils optionally having at least one dimethicone fragment corresponding to formula (S-VII) below, and mixtures thereof:

(S-VII)

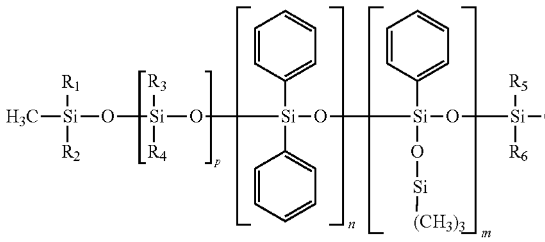

in which:

$R_1$ to $R_6$, independently of each other, are saturated or unsaturated, linear, cyclic or branched $C_1$-$C_{30}$ hydrocarbon-based radicals, a preferably $C_6$-$C_{14}$ aryl radical or an aralkyl radical, the alkyl part of which is $C_1$-$C_3$ alkyl, m, n and p are, independently of each other, integers between 0 and 100, with the proviso that the sum n+m is between 1 and 100.

Preferably, $R_1$ to $R_6$, independently of each other, represent a $C_1$-$C_{20}$, in particular $C_1$-$C_{18}$, hydrocarbon-based, preferably alkyl, radical, or a $C_6$-$C_{14}$ aryl radical which is monocyclic (preferably $C_6$) or polycyclic and in particular $C_{10}$-$C_{13}$, or an aralkyl radical (preferably the aryl part is $C_6$ aryl; the alkyl part is $C_1$-$C_3$ alkyl).

Preferably, $R_1$ to $R_6$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may in particular be identical, and in addition may be a methyl radical. Preferably, m=1 or 2 or 3, and/or n=0 and/or p=0 or 1 can be applied, in formula (S-VII).

According to one particular embodiment, the non-volatile phenyl silicone oil is chosen from non-volatile phenyl silicone oils having at least one dimethicone fragment.

Preferably, such oils correspond to compounds of formula (S-VII) in which:

A) m=0 and n and p are, independently of each other, integers between 1 and 100

Preferably, $R_1$ to $R_6$ are methyl radicals.

According to this embodiment, the silicone oil is preferably chosen from a diphenyl dimethicone such as KF-54 from Shin Etsu (400 cSt), KF54HV from Shin Etsu (5000 cSt), KF-50-300CS from Shin Etsu (300 cSt), KF-53 from Shin Etsu (175 cSt) or KF-50-100CS from Shin Etsu (100 cSt).

B) p is between 1 and 100, the sum n+m is between 1 and 100, and n=0

These phenyl silicone oils optionally having at least one dimethicone fragment correspond more particularly to formula (S-VIII) below:

(S-VIII)

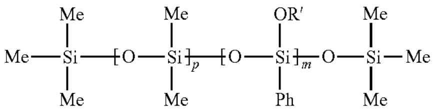

in which Me is methyl and Ph is phenyl, OR' represents a group —$OSiMe_3$ and p is 0 or is between 1 and 1000, and m is between 1 and 1000. In particular, m and p are such that the compound (S-VIII) is a non-volatile oil.

According to a first embodiment of non-volatile phenyl silicone having at least one dimethicone fragment, p is between 1 and 1000 and m is more particularly such that the compound (S-VIII) is a non-volatile oil. Trimethylsiloxyphenyl dimethicone, sold in particular under the reference Belsil PDM 1000 by the company Wacker, may, for example, be used.

According to a second embodiment of non-volatile phenyl silicone not having a dimethicone fragment, p is equal to 0 and m is between 1 and 1000, and in particular is such that the compound (S-VIII) is a non-volatile oil.

Phenyltrimethylsiloxytrisiloxane, sold in particular under the reference Dow Corning 556 Cosmetic Grade Fluid (DC556), may, for example, be used.

ii) non-volatile phenyl silicone oils not having a dimethicone fragment corresponding to formula (S-IX) below, and mixtures thereof:

(S-IX)

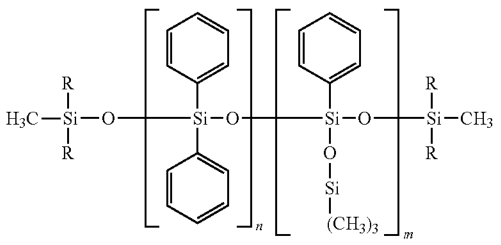

in which:

R, independently of each other, are saturated or unsaturated, linear, cyclic or branched $C_1$-$C_{30}$ hydrocarbon-based radicals, preferably R is a $C_1$-$C_{30}$ alkyl radical, a preferably $C_6$-$C_{14}$ aryl radical, or an aralkyl radical, the alkyl part of which is $C_1$-$C_3$ alkyl, m and n are, independently of each other, integers between 0 and 100, with the proviso that the sum n+m is between 1 and 100.

Preferably, R, independently of each other, represent a saturated or unsaturated, preferably saturated, linear or branched $C_1$-$C_{30}$ hydrocarbon-based radical, and in particular a preferably saturated, $C_1$-$C_{20}$, in particular $C_1$-$C_{18}$ and more particularly $C_4$-$C_{10}$, hydrocarbon-based radical, a monocyclic or polycyclic $C_6$-$C_{14}$, and in particular $C_{10}$-$C_{13}$, aryl radical, or an aralkyl radical of which preferably the aryl part is $C_6$ aryl and the alkyl part is $C_1$-$C_3$ alkyl.

Preferably, the groups R may each represent a methyl, ethyl, propyl, butyl, isopropyl, decyl, dodecyl or octadecyl radical, or alternatively a phenyl, tolyl, benzyl or phenethyl radical.

The groups R may in particular be identical, and in addition may be a methyl radical.

Preferably, m=1 or 2 or 3, and/or n=0 and/or p=0 or 1 can be applied, in formula (S-IX).

According to one preferred embodiment, n is an integer between 0 and 100 and m is an integer between 1 and 100, with the proviso that the sum n+m is between 1 and 100, in formula (S-IX). Preferably, R is a methyl radical.

According to one embodiment, the non-volatile phenyl silicone oil is preferably chosen from phenyl trimethicones (when n=0) such as DC556 from Dow Corning (22.5 cSt), or else from diphenylsiloxyphenyl trimethicone oil (when m and n are between 1 and 100) such as KF56 A from Shin Etsu, or the Silbione 70663V30 oil from Rhône-Poulenc (28 cSt). The values in parentheses represent the viscosities at 25° C.

e) phenyl silicone oils optionally having at least one dimethicone fragment corresponding to the following formula, and mixtures thereof:

(S-X)

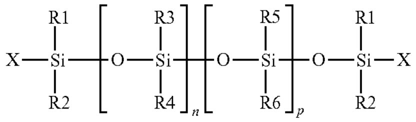

in which:

$R_1$, $R_2$, $R_5$ and $R_6$, which may be identical or different, are an alkyl radical containing 1 to 6 carbon atoms, $R_3$ and $R_4$, which may be identical or different, are an alkyl radical containing from 1 to 6 carbon atoms or an aryl radical (preferably $C_6$-$C_{14}$), with the proviso that at least one of $R_3$ and $R_4$ is a phenyl radical, X is an alkyl radical containing from 1 to 6 carbon atoms, a hydroxyl radical or a vinyl radical, n and p being an integer greater than or equal to 1, chosen so as to give the oil a weight-average molecular weight of less than 200000 g/mol, preferably less than 150000 g/mol and more preferably less than 100000 g/mol.

f) and a mixture thereof

According to a preferred embodiment of the invention, the composition according to the invention further comprises one or more non-volatile silicone oils; more preferably the non-volatile silicone oil(s) is/are chosen from the non-volatile phenyl silicone oils, the non-volatile non-phenyl silicone oils, and mixtures thereof; even more preferably chosen from the non-volatile non-phenyl silicone oils; better still chosen from non-volatile polyalkylsiloxanes such as non-volatile polydimethylsiloxanes containing trimethylsilyl or dimethylsilanol end groups.

According to this embodiment, the non-volatile silicone oil(s) preferably represent(s) from 0.1 to 30% by weight, more preferably from 1 to 25% by weight, even more preferably from 5 to 20% by weight, relative to the total weight of the composition.

Preferably, when the non-volatile silicone oil(s) is/are present in the according to the invention, the non-volatile silicone oil(s) represent(s) from 0.1 to 30% by weight, more preferably from 1 to 25% by weight, even more preferably from 5 to 20% by weight, relative to the total weight of the composition.

Preferably, when the polyalkylsiloxane(s) is/are present in the according to the invention, the polyalkylsiloxane(s) represent(s) from 0.1 to 30% by weight, more preferably from 1 to 25% by weight, even more preferably from 5 to 20% by weight, relative to the total weight of the composition.

The composition may comprise a cosmetically acceptable medium. The cosmetically acceptable medium that can be used in the compositions of the invention may comprise water, one or more organic solvents, or a mixture thereof.

By way of examples of organic solvents, use may especially be made of those which are liquid at 25° C., especially $1.013\times10^5$ Pa, especially water-soluble, such as the $C_1$-$C_7$ alcohols, and in particular the aliphatic or aromatic monoalcohols of $C_1$-$C_7$, $C_3$-$C_7$ polyols and ethers of $C_3$-$C_7$ polyols, which can therefore be used alone or mixed with water. Advantageously, the organic solvent may be chosen from ethanol, isopropanol and mixtures thereof.

Preferably, the composition according to the invention is anhydrous.

The term "anhydrous composition" means a composition containing less than 2% by weight of water, preferably less than 1% by weight of water, more preferably less than 0.5% by weight of water relative to total weight of the composition, and even better a composition which does not contain water. In this type of composition, any water present is not added during the preparation of the composition but corresponding to the residual water provided by the mixed ingredients.

Preferably, the pH of the composition is between 1.5 and 11, more preferably between 3 and 9, even more preferably between 4 and 8, better still between 4 and 7.5.

The pH of these compositions can be adjusted to the desired value by means of alkalinizing agents or acidifying agents. Among the alkalinizing agents that may be mentioned, for example, are ammonia, alkanolamines or mineral or organic hydroxides. Among the acidifying agents, mention may be made, for example, of mineral or organic acids such as hydrochloric acid, orthophosphoric acid, carboxylic acids, for example acetic acid, tartaric acid, citric acid, lactic acid, sulfonic acids.

The composition according to the invention may also contain cosmetics additives, such as thickening agents, preserving agents, perfumes, cationic, anionic and/or nonionic surfactants, amphoteric and/or cationic polymers, pearlescent agents.

These additives may be present in the composition according to the invention in an amount ranging from 0 to 20% by weight relative to the total weight of the composition.

The skilled in the art person will take care to choose these optional additives and their amounts so that they do not adversely affect the properties of the compositions according to the present invention.

The composition according to the invention may be in the form of a conditioning oil.

Preferably, the composition according to the invention is used on dyed keratin fibres, in particular on dyed human keratin fibres such as dyed hair.

The use of the composition can be done on wet or dry hair, in rinsed or not rinsed mode.

According to a particularly preferred embodiment of the invention, the composition comprises:

i) at least 5% by weight relative to the total weight of the composition, of caprylic/capric triglyceride;

ii) at least 10% by weight relative to the total weight of the composition, of isododecane or decamethylcyclopentasiloxane;

iii) one or more lipophilic dyes chosen from D&C Violet 2 (C.I. 60725), beta-carotene (C.I. 75130), Green 6 (C.I. 61565), astaxanthin, and mixtures thereof; and iv) optionally one or more non-volatile polyalkylsiloxanes.

The subject-matter of the invention is also a method for conditioning keratin fibres, in particular human keratin fibres such as the hair, comprising at least a step of applying onto said keratin fibres a composition according to the invention as described previously.

Preferably, the method according to the invention is a method for conditioning dyed keratin fibres, in particular dyed human keratin fibres such as dyed hair.

According to a particular embodiment of the invention, after the step(s) of applying onto said keratin fibres a composition according to the invention as described previously, the composition according to the invention is left on said keratin fibres for at least 60 minutes, more preferably for at least four hours. In other words, the composition on the said keratin fibres is not rinsed before at least 60 minutes after its application; more preferably before at least four hours after its application.

According to another particular embodiment of the invention, a step of rinsing the keratin fibres can be implemented after the step(s) of applying onto said keratin fibres a composition according to the invention as described previously.

The invention also relates to the use of the composition according to the invention as described previously, for conditioning keratin fibers, in particular human keratin fibres such as the hair.

Preferably, the composition according to the invention as described previously is used for conditioning dyed keratin fibres, in particular dyed human keratin fibres such as dyed hair The following examples are given by way of illustration of the present invention and shall not be interpreted as limiting the scope.

EXAMPLES

The compositions A and B according to the invention containing the ingredients hereunder were prepared, with all amounts expressed by percentages by weight of active matter with regard to the total weight of each composition.

Composition A (Invention):

| Ingredients | Amounts |
|---|---|
| CAPRYLIC/CAPRIC TRIGLYCERIDE | 20.0 |
| BETA-CAROTENE (C.I. 75130) | 0.008 |
| D&C VIOLET 2 (C.I. 60725) | 0.006 |
| DIMETHICONOL | 5.88 |
| FRAGRANCE | 0.4 |
| CYCLOPENTASILOXANE | Qs 100 |

Composition B (Invention):

| Ingredients | Amounts |
|---|---|
| CAPRYLIC/CAPRIC TRIGLYCERIDE | 20.0 |
| BETA-CAROTENE (C.I. 75130) | 0.008 |
| D&C VIOLET 2 (C.I. 60725) | 0.006 |
| DIMETHICONE | 8 |
| DIMETHICONOL | 6 |
| FRAGRANCE | 0.4 |
| ISODODECANE | Qs 100 |

0.4 grams of composition A and B were applied, respectively to a 1 gram lock of Asian bleached hair sensitized (SA 20).

The locks were gently massaged from the root to the tip about 6 times between two fingers for 15 seconds.

It is observed that the locks treated with one of the composition A or B according to the invention are easier to detangle and present a better colour uptake, more shine, more smooth, and less frizz, than a lock of untreated hair.

In addition, the locks treated with one of the composition A or B according to the invention do not leave stains on the hands, nor on the skin.

The invention claimed is:

1. A hair conditioning oil composition comprising:

i) from 10% to 35% by weight relative to the total weight of the composition, of one or more non-volatile oils chosen from esters of glycerol and of one or more identical or different, saturated or unsaturated, fatty acids containing 4 to 30 carbon atoms;

ii) at least 50% by weight relative to the total weight of the composition, of one or more volatile oils;

iii) from 0.0001% to 10% by weight, relative to the total weight of the composition, of one or more lipophilic dyes, iv) from 5% to 20% by weight, relative to the total weight of the composition, of one or more non-volatile polyalkylsiloxanes containing dimethylsilanol end groups.

2. The hair conditioning oil composition according to claim 1, characterized in that the non-volatile oils i) is/are chosen from esters of glycerol and of one or more fatty acids containing 6 to 24 carbon atoms.

3. The hair conditioning oil composition according to claim 1, characterized in that the non-volatile oil(s) i) is/are chosen from caprylic/capric triglyceride, olive oil, macadamia *ternifolia* seed oil, castor oil, sunflower oil, soybean oil, sesame oil, apricot kernel oil, coriander seed oil, limnanthes alba seed oil, nigella *sativa* seed oil, pentaclethra macroloba seed oil, *Adansonia digitata* seed oil, *Mauritia flexuosa* oil, *lunaria annua* oil, pennycress oil, *cuphea* oil, and mixtures thereof.

4. The hair conditioning oil composition according to claim 1, characterized in that the volatile oil(s) ii) is/are chosen from the hydrocarbon-based volatile oils, the volatile silicone oils, and mixtures thereof.

5. The hair conditioning oil composition according to claim 1, characterized in that the volatile oil(s) ii) represent(s) from 50% to 90% by weight, relative to the total weight of the composition.

6. The hair conditioning oil composition according to claim 1, characterized in that it comprises a weight ratio of the content of non-volatile oil(s) i) to the content of the volatile oil(s) ii), which is between 0.1 and 0.9.

7. The hair conditioning oil composition according to claim 1, characterized in that the lipophilic dye(s) iii) is/are chosen from DC Red 17, DC Red 21, DC Red 27, DC Green 6, DC Yellow 11, DC Violet 2, DC Orange 5, Sudan Red, Sudan brown, quinoline yellow, annatto, curcumin, carotenes, xanthophylls, lipophilic green dyes and mixtures thereof.

8. The hair conditioning oil composition according to claim 1, characterized in that it is anhydrous.

9. The hair conditioning oil composition according to claim 1, characterized in that the volatile oil(s) ii) is/are chosen from C8-C16 isoalkanes, linear C8-C16 alkanes, volatile linear alkyltrisiloxane oils of general formula (I):

(I)

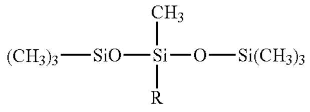

in which R represents an alkyl group comprising from 2 to 4 carbon atoms, one or more hydrogen atoms of which may be replaced with a fluorine or chlorine atom;

volatile linear or cyclic silicone oils different from the volatile linear alkyltrisiloxane oils of general formula (I), and mixtures thereof.

10. The hair conditioning oil composition according to claim 1, characterized in that the volatile oil(s) ii) is/are chosen from isododecane or decamethylcyclopentasiloxane.

11. The hair conditioning oil composition according to claim 1, characterized in that the non-volatile oil i) is caprylic/capric triglyceride.

12. Method for conditioning the hair, comprising at least a step of applying onto the hair a hair conditioning oil composition as defined in claim 1.

13. Method according to claim 12, for conditioning dyed hair.

* * * * *